US010010384B2

(12) United States Patent
Richard

(10) Patent No.: US 10,010,384 B2
(45) Date of Patent: Jul. 3, 2018

(54) DENTAL COMPONENT FOR THE INDIVIDUAL PROSTHETIC RECONSTRUCTION OF A TOOTH

(71) Applicant: ANTHOGYR, Sallanches (FR)

(72) Inventor: Hervé Richard, Notre Dame de Bellecombe (FR)

(73) Assignee: ANTHOGYR, Sallanches (FR)

( * ) Notice: Subject to any disclaimer, the term of this patent is extended or adjusted under 35 U.S.C. 154(b) by 0 days.

(21) Appl. No.: 15/408,584

(22) Filed: Jan. 18, 2017

(65) Prior Publication Data

US 2017/0224447 A1   Aug. 10, 2017

(30) Foreign Application Priority Data

Feb. 5, 2016   (FR) ..................... 16 50935

(51) Int. Cl.
*A61C 8/00* (2006.01)
*A61C 13/083* (2006.01)
*A61C 13/09* (2006.01)
*A61C 13/00* (2006.01)

(52) U.S. Cl.
CPC .......... *A61C 8/0063* (2013.01); *A61C 8/0056* (2013.01); *A61C 8/0057* (2013.01); *A61C 8/0062* (2013.01); *A61C 8/0066* (2013.01); *A61C 8/0068* (2013.01); *A61C 8/0069* (2013.01); *A61C 13/0022* (2013.01); *A61C 13/083* (2013.01); *A61C 13/09* (2013.01)

(58) Field of Classification Search
CPC ... A61C 8/0063; A61C 8/0056; A61C 8/0057; A61C 8/0062; A61C 8/0066; A61C 8/0068; A61C 8/0069; A61C 13/0022; A61C 13/083; A61C 13/09
See application file for complete search history.

(56) References Cited

U.S. PATENT DOCUMENTS

| | | | | |
|---|---|---|---|---|
| 5,087,199 A * | 2/1992 | Lazarof | ................ | A61C 8/0033 433/173 |
| 5,733,122 A * | 3/1998 | Gordon | ................ | A61C 8/005 433/172 |
| 5,931,674 A * | 8/1999 | Hanosh | ................ | A61C 8/0033 433/173 |
| 5,947,733 A * | 9/1999 | Sutter | ................ | A61C 8/005 433/173 |
| 6,142,782 A * | 11/2000 | Lazarof | ................ | A61C 8/0001 433/174 |
| 6,350,126 B1 * | 2/2002 | Levisman | ............ | A61C 8/0033 433/1 |

(Continued)

FOREIGN PATENT DOCUMENTS

EP   2053985 B1   5/2009
EP   2127612 A1   12/2009

(Continued)

*Primary Examiner* — Nicholas Lucchesi
(74) *Attorney, Agent, or Firm* — William H. Eilberg

(57) ABSTRACT

Dental component for the individual prosthetic reconstruction of a tooth, intended to be received on a dental implant, including a first element with an angled through-passage, and a second element intended to be received against or in a dental implant. Assembly features between the first and second elements make it possible effectively to limit the removal of material to be performed in the first element in order to create the angled through-passage.

13 Claims, 9 Drawing Sheets

(56) References Cited

U.S. PATENT DOCUMENTS

| | | | | |
|---|---|---|---|---|
| 6,506,051 | B2* | 1/2003 | Levisman | A61C 8/0033 |
| | | | | 433/173 |
| 7,845,946 | B2* | 12/2010 | Brajnovic | A61C 8/0048 |
| | | | | 433/174 |
| 8,167,619 | B2* | 5/2012 | Vachtenberg | A61C 8/0033 |
| | | | | 433/173 |
| 8,696,720 | B2* | 4/2014 | Lazarof | A61B 17/8625 |
| | | | | 606/313 |
| 9,265,591 | B1* | 2/2016 | Gittleman | A61C 1/084 |
| 2006/0014120 | A1 | 1/2006 | Sapian | |
| 2008/0241790 | A1* | 10/2008 | Gittleman | A61C 8/0053 |
| | | | | 433/174 |
| 2008/0261174 | A1* | 10/2008 | Gittleman | A61C 8/0048 |
| | | | | 433/172 |
| 2014/0178836 | A1 | 6/2014 | Haus | |

FOREIGN PATENT DOCUMENTS

| | | |
|---|---|---|
| EP | 2607722 B1 | 6/2013 |
| GB | 2509136 A | 6/2014 |
| WO | 2012163528 A1 | 12/2012 |
| WO | 2013004387 A1 | 1/2013 |

\* cited by examiner

DENTAL COMPONENT FOR THE INDIVIDUAL PROSTHETIC RECONSTRUCTION OF A TOOTH

The present invention relates to the field of dentistry, and relates more particularly to a dental component for the individual prosthetic reconstruction of a tooth, said dental component being intended to be received on a dental implant.

In the context of the individual prosthetic reconstruction of a tooth, recourse is often had to a prosthesis that is transfixed, which means to say it is provided with a through-passage that allows the prosthesis to be fixed by a fixing screw (passing through the prosthesis) to a dental implant which is osteointegrated into the jaw of the patient.

Various types of transfixed prostheses are known:

those that comprise a core (notably made of metal) on which the prosthetist performs stratification, leaving the through-passage open (by applying a material in one or more layers to give an appearance that is as close as possible to that of a natural tooth);

those that comprise a ceramic core (machined from a block of ceramic or produced by sintering a ceramic powder in particular), possibly coated by the prosthetist with one or more very light layers of texture or color to yield an appearance as close as possible to that of a natural tooth.

Depending on the position of the dental implant fixed into the jaw of the patient, it is often necessary to adjust with care the location of the coronal emergence of the well allowing the passage of the fixing screw. The issue is actually one of being able, despite the shortage of space available in the mouth of the patient, to access the fixing screw using a screw turning tool. It is also important for the coronal emergence of the access well to be positioned away from the parts of the tooth that are active during chewing (cusps).

Dental prostheses with a core provided with an angled through-passage comprising a first passage portion extending from a proximal end of the first element along a first longitudinal axis and comprising a second passage portion secant with the first passage portion, the first and second passage portions forming a non-zero angle between them, are known for that purpose (see notably documents EP 2 053 985, WO 2013/004387 and US 2014/0178836). The term "proximal" is intended to qualify a part of an element that is intended to be closer to the patient during use thereof than another part that will be qualified as "distal".

In those documents, the angled through-passage allows the fixing screw to be inserted and routed along a curved pathway via a path that begins in the second passage portion and continues into the first passage portion at the end of which there is a seat against which the screw head comes to bear in abutment. This curved pathway of the screw requires a fairly significant removal of material from the core of the prosthesis, which reduces the mechanical strength thereof.

Document GB 2 509 136 describes a dental component comprising a first element of the ceramic core type and a second element intended to engage in the first element and in a dental implant in order to rotationally index the first element with respect to the dental implant. The second element comprises longitudinal fins able to provide a precarious connection between the first and second elements. The first element of the ceramic core type comprises an angled through-passage allowing the fixing screw to be inserted and routed along a curved pathway via a path that begins in the second passage portion and continues into the first passage portion at the end of which there is a seat against which the screw head comes to bear in abutment. This curved pathway followed by the screw requires a fairly significant removal of material from the core of the prosthesis, thereby reducing the mechanical strength of the first element.

Document EP 2 127 612 A1 relates to an angled dental abutment for multiple prosthetic reconstruction. This angled dental abutment comprises a first passage which is rectilinear and passes all the way through the abutment. A second passage, which is inclined, intersects an intermediate portion of the rectilinear first through-passage. This structure involving two passages that form an intersection requires a significant removal of material, which causes a weakening of the mechanical strength.

A problem put forward by the present invention is to provide another solution that makes it possible to fix to a dental implant a transfixed dental prosthesis comprising a core on which stratification is performed or comprising a ceramic core, while allowing recourse to be had to a through-passage that is angled in order to take account of the constraints on orienting the osteointegrated dental implant, on accessibility and on preserving the active parts of the tooth, without by so doing needlessly lowering the mechanical strength of said transfixed dental prosthesis.

In order to achieve these objectives as well as others, the invention proposes a dental component for the individual prosthetic reconstruction of a tooth, intended to be received on a dental implant, comprising:

a first element, of the core type on which stratification is performed, or of the ceramic core type, said first element having a first through-passage made up of first and second successive passage portions, said first passage portion extending from a proximal end of the first element along a first longitudinal axis, and said second passage portion extending the first passage portion in such a way that the first and second passage portions form between them a non-zero angle, a second element with a second through-passage extending along a second longitudinal axis, comprising a distal end intended to receive in abutment the first element and comprising a proximal end intended to bear in axial abutment against or intended to penetrate into said dental implant, a fixing screw comprising a screw head from which there extends a screw shank provided with a threaded portion intended to be received by screwing in said dental implant, several longitudinal fins extending along the second longitudinal axis from and away from the distal end of the second element, each longitudinal fin comprising a free distal part that can be moved radially away from the second longitudinal axis; according to the invention:

the screw shank is able to pass through the second element by being received between the longitudinal fins and into the second through-passage in order to screw into the dental implant, whereas the screw head then comes to rest in axial abutment against the free distal parts of the longitudinal fins to retain the second element on the dental implant, the first passage portion of the first element has transverse dimensions allowing the longitudinal fins and the screw head to be received by axial penetration along the first longitudinal axis from the proximal end of the first element, the screw head and the free distal parts of the longitudinal fins are configured in such a way that, when the first element receives the longitudinal fins and the screw head, a relative translational displacement of the fixing screw toward the second element along the second longitudinal axis causes a radial displacement of the free distal parts of the longitudinal fins away from the second longitudinal axis in order to press them against the lateral wall of the first passage portion in order to oppose a withdrawal of the first element away from the second element, the second passage portion of the first element has transverse dimensions smaller than those of the first passage portion, but sufficient for the passage of a tool that allows the fixing screw to be turned about the second longitudinal axis.

Such a dental component allows the satisfactory fixing to a dental implant of the first element comprising an angled passage, which first element is a dental prosthesis core intended to be stratified or a dental prosthesis monoblock (sintered or machined) ceramic core, while at the same time duly taking account of the constraints on the orientation of the osteointegrated dental implant, on the accessibility in the mouth, and on the preserving of the active parts of the tooth. When the screw is placed under tension by screwing it into the dental implant, the screw head is pulled toward the second element along the second longitudinal axis and causes a radial displacement of the free distal parts of the longitudinal fins away from the second longitudinal axis. This has the effect of pressing the free distal parts of the longitudinal fins against the lateral wall of the first passage portion, and therefore of opposing withdrawal of the first element away from the second element.

The removal of material that needs to be performed in the first element in order to create the angled passage is less, notably with respect what is done in documents GB 2 509 136, EP 2 053 985, WO 2013/004387 and US 2014/0178836. Specifically, the screw is received only in the first passage portion and no longer passes through the second passage portion. Only the tool used to turn the fixing screw passes through the second passage, portion, and the penetrating part of the tool has no head. The first and second passage portions can thus have relatively simple (substantially cylindrical) shapes. In addition, although the cross section of the first passage portion has a necessity to have dimensions that allow the insertion of the screw head, the second passage portion may itself have transverse dimensions smaller than those of the first passage portion, sufficient only for the passage of a tool that allows the screw to be turned about the second longitudinal axis. In order to turn the screw, it is possible for example to have recourse to the use of a tool that allows angling with respect to the screw head when screwing or unscrewing, as described for example in document EP 2 607 722.

Finally, in the present invention, the first and second passage portions follow on from one another and thus form an angled first through-passage more or less in the form of a "bend". Such a structure allows less material to have to be removed, therefore making it possible to reduce the mechanical strength to a lesser extent, than the intersection between two passages as used in document EP 2 127 512 A1.

For preference, the screw head may comprise a substantially frustoconical contact surface intended to come into contact against the free distal parts of the longitudinal fins and/or the free distal parts of the longitudinal fins comprise respective contact surfaces intended to receive in abutment the screw head and forming a substantially frustoconical surface.

Thus, a radial displacement of the free distal parts of the longitudinal fins away from the second longitudinal axis when the screw is displaced relatively in translation toward the second element along the second longitudinal axis is obtained in a simple and effective way.

Advantageously, the dental component may comprise rotational-indexing means for indexing the first and second elements about the first longitudinal axis. This then limits the risk of movement between the first and second elements, it being possible for such movement to lead to premature failure of one or other element (notably through wear).

For preference, the second element may comprise a proximal appendage of non-circular cross section which is intended to be received in a housing of non-circular cross section of the dental implant. This then limits the risk of movement between the second element and the dental implant, it being possible for such movement to lead to premature failure or one or other element (notably through wear). This also guarantees a fixed and determined orientation of the dental component with respect to the dental implant.

Advantageously, the first element may comprise a groove intended to receive the free distal parts of the longitudinal fins during their radial displacement away from the second longitudinal axis. Radial engagement of the free distal parts of the longitudinal fins in the groove provides improved retention of the first element on the second element.

For preference, engagement of the free distal parts of the longitudinal fins in the groove may be reversible. The reversible nature of the engagement of the longitudinal fins in the groove allows the prosthetist to assemble and separate the first element in relation to the second element and the fixing screw easily and on a number of occasions so that only the first element is placed in the oven while it is being stratified. This then avoids oxidation degradation of the second element and of the fixing screw.

For preference, the groove and or the free distal parts of the longitudinal fins may comprise respective contact surfaces which are configured in such a way that the radial pressing of the free distal parts of the longitudinal fins against the groove causes, along the first longitudinal axis, a pressing of the proximal end of the first element against the distal end of the second element.

The pressing of the proximal end of the first element against the distal end of the second element effectively limits the risk of bacteria entering and growing at the interface between the first and second elements.

Advantageously, it may be planned that:

the free distal parts of the longitudinal fins are displaceable between a closed-up position in which they are radially distant from the second longitudinal axis by a first distance, and a spread position in which they are radially distant from the second longitudinal axis by a second distance greater than the first distance, the free distal parts of the longitudinal fins are elastically returned to the spread position, the groove and the longitudinal fins are dimensioned and configured in such a way that the free distal parts of the longitudinal fins are received by snap-fastening in the groove when the first passage portion receives the longitudinal fins and the screw head by axial penetration along the first longitudinal axis.

The snap-fastening of the longitudinal fins into the groove allows the first and second elements, with the fixing screw trapped between them, to be secured precariously (because reversibly), but sufficiently. The prosthetist may thus send the dental surgeon a unitary subassembly comprising the first and second elements and the fixing screw all assembled. The dental surgeon can then introduce the unitary subassembly into the patient's mouth in a single action and engage it on the osteointegrated dental implant. That reduces the number of elements that need to be handled, the risk of losing components (notably the screw) and the risk of incorrect manipulation.

According to another aspect, the present invention proposes a dental assembly comprising:
a dental component as described hereinabove,
a dental implant comprising an internal housing with a threaded portion intended to receive the fixing screw by screwing.

Advantageously, the second element may be configured in such a way as to attach and fix the first element to the dental implant without contact between the first element and the dental implant. The second element thus acts as a spacer between the first element and the dental implant. This then prevents any relative micromovements between the first element and the dental implant from leading premature wearing of the dental implant which is osteointegrated and which it is therefore necessary to avoid having to replace. All this is of particular importance when the dental implant is made not of ceramic (but, for example, of metal, notably titanium or titanium alloy). If micromovements between the first element and the second element occur, leading to premature wearing of the latter, the second element can easily and quickly be replaced. Further, if the second element wears, generating debris, this debris will be generated in a region that is distant from the bone, thereby limiting the risk of necrosis of the bone around the dental implant.

According to yet another aspect, the present invention proposes a method for the ex-vivo assembly of a dental component as described hereinabove with the free distal parts of the longitudinal fins being snap-fastened into a groove, said method comprising the following steps
a) inserting the screw shank between the longitudinal fins and into the second through-passage,
b) inserting into the first passage portion the longitudinal fins and the screw head through an axial translational movement along the first longitudinal axis from the proximal end of the first element until the free distal parts of the longitudinal fins snap-fasten into the groove.

Further objects, features and advantages of the present invention will become apparent from the following description of some particular embodiments, given with reference to the attached figures among which:

FIGS. 1 to 10 illustrate two embodiments of a dental component 1 according to the invention. A first embodiment is illustrated in FIGS. 1 to 9, and a second embodiment is illustrated in FIG. 10.

Figure 1:
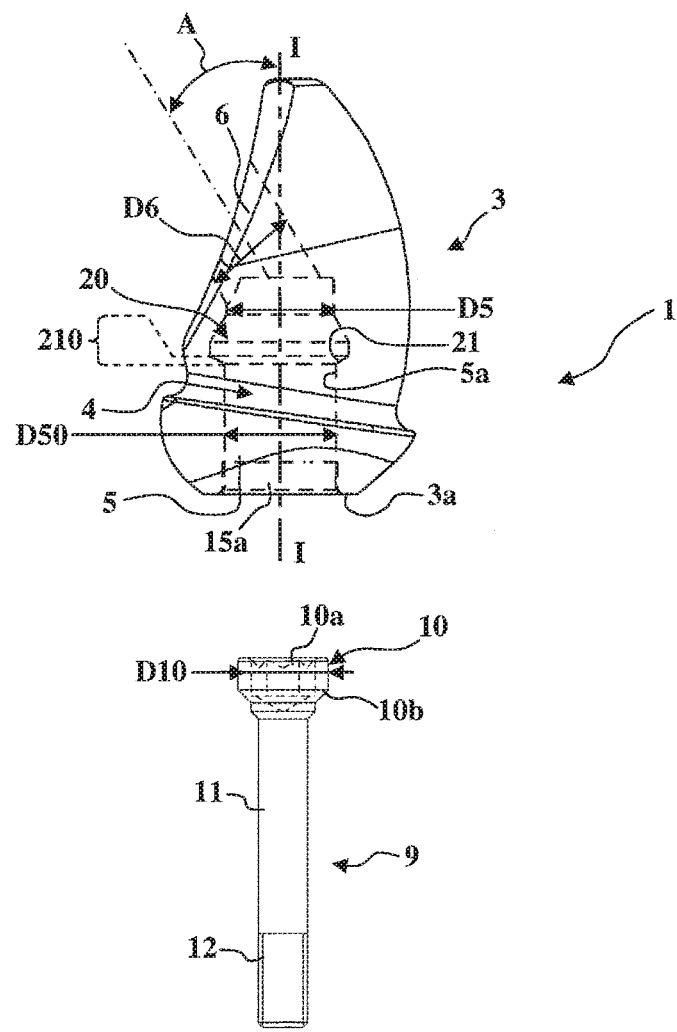
FIG. 1 is a side view of a dental component according to a first embodiment, with a first element of the dental prosthesis core type that is intended to be stratified.
Figure 1:
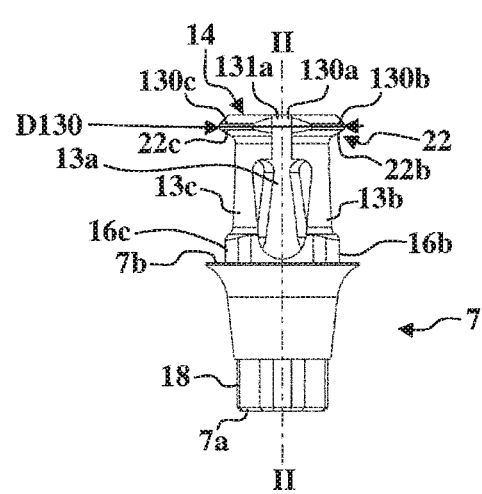
Figure 2:
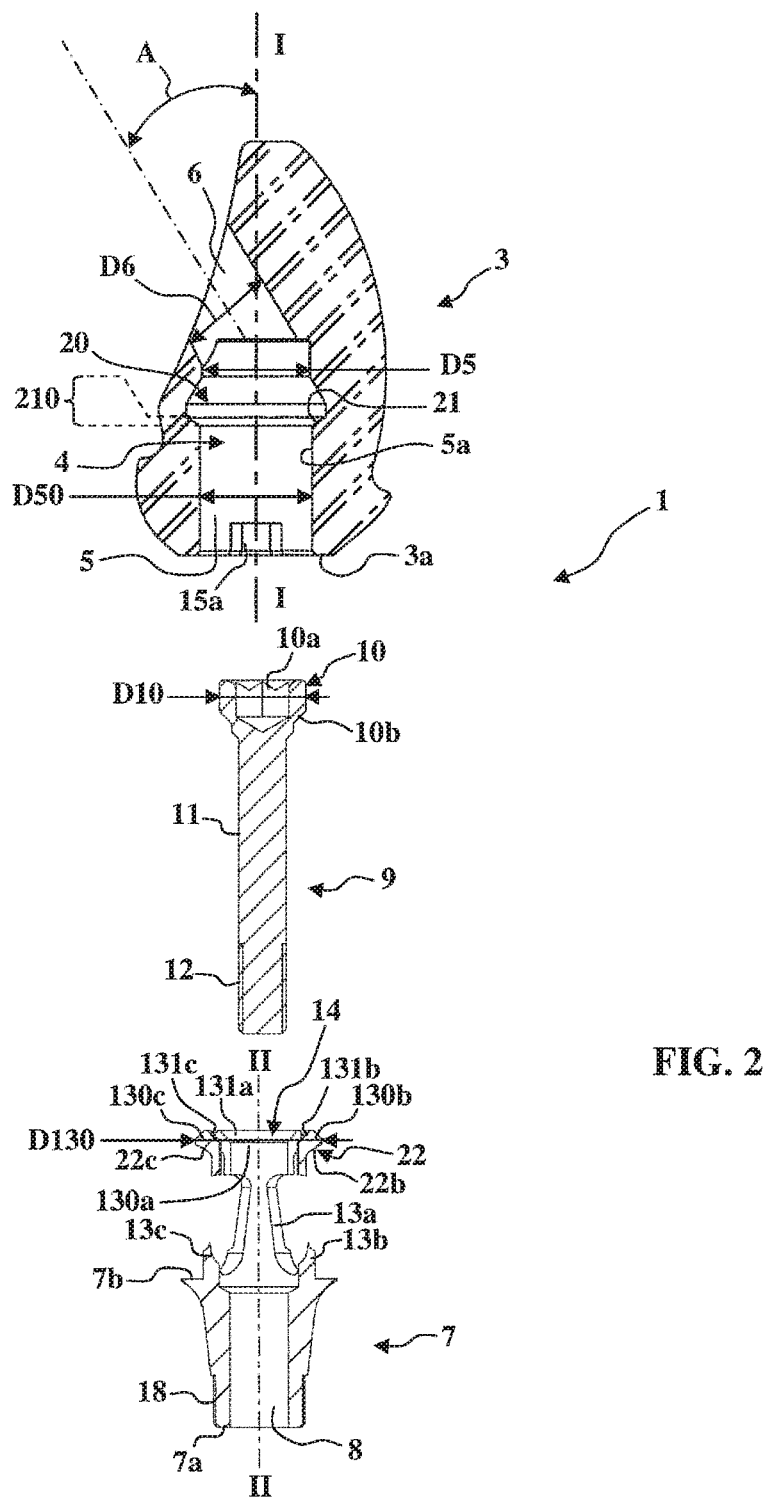
FIG. 2 is a side and sectional view of the dental component of FIG. 1.
Figure 8:
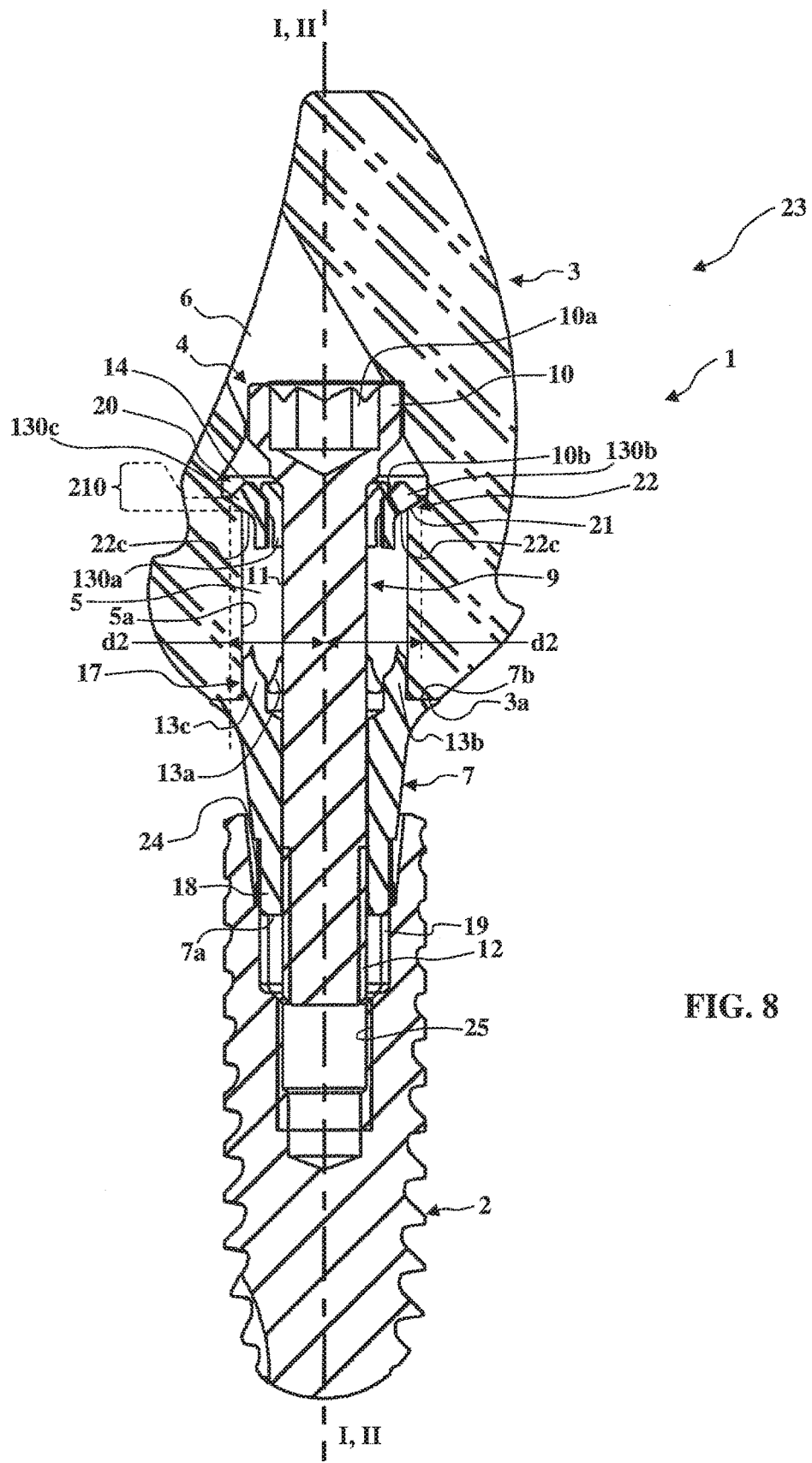
FIG. 8 is a view in cross section and from the side of the dental component of FIG. 1 during the course of assembly on a dental implant to form a dental assembly.

It may be seen more particularly from FIGS. 1 and 2 that the dental component 1 for the individual prosthetic reconstruction of a tooth, intended to be received on a dental implant 2 (FIG. 8), comprises:
a first element 3 with a first through-passage 4 made up of first 5 and second 6 successive passage portions, said first passage portion 5 extending from a proximal end 3a of the first element 3 along a first longitudinal axis I-I, and said second passage portion 6 extending the first passage portion 5 in such a way that the first and second passage portions 5 and 6 form a non-zero angle A between them,
a second element 7 with a second through-passage 8 extending along a second longitudinal axis II-II, comprising a distal end 7b intended to receive the first element 3 in abutment and comprising a proximal end 7a intended to bear in axial abutment against or intended to penetrate into said dental implant 2,
a fixing screw 9 comprising a screw head 10 from which there extends a screw shank 11 equipped with a threaded portion 12 intended to be received by screwing in said dental implant 2 (FIG. 8).

Figure 6:
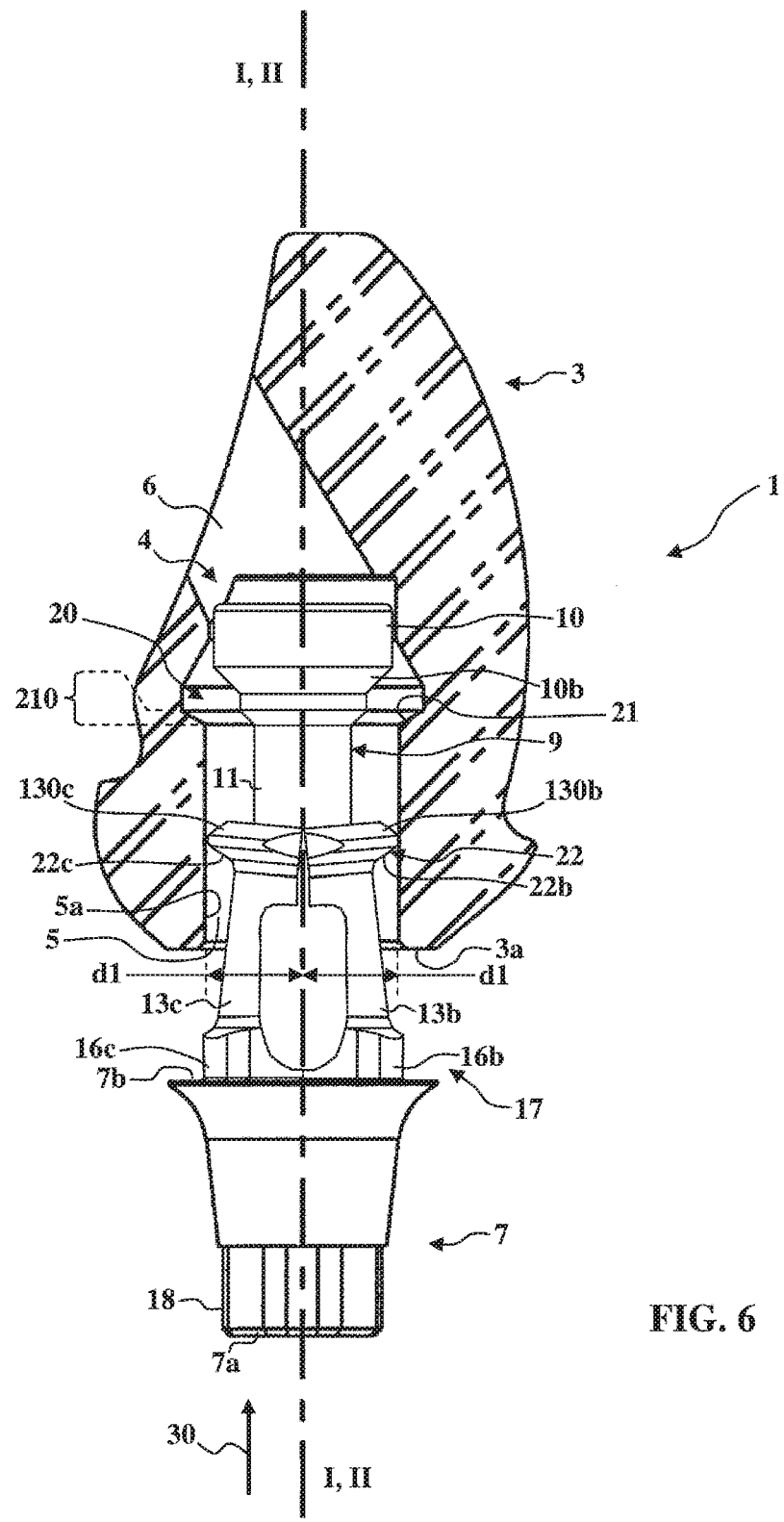
FIG. 6 is a view in partial cross section and from the side of the dental component of FIG. 1 during the course of assembly, at a later stage to the stage illustrated in FIG. 5.
Figure 9:
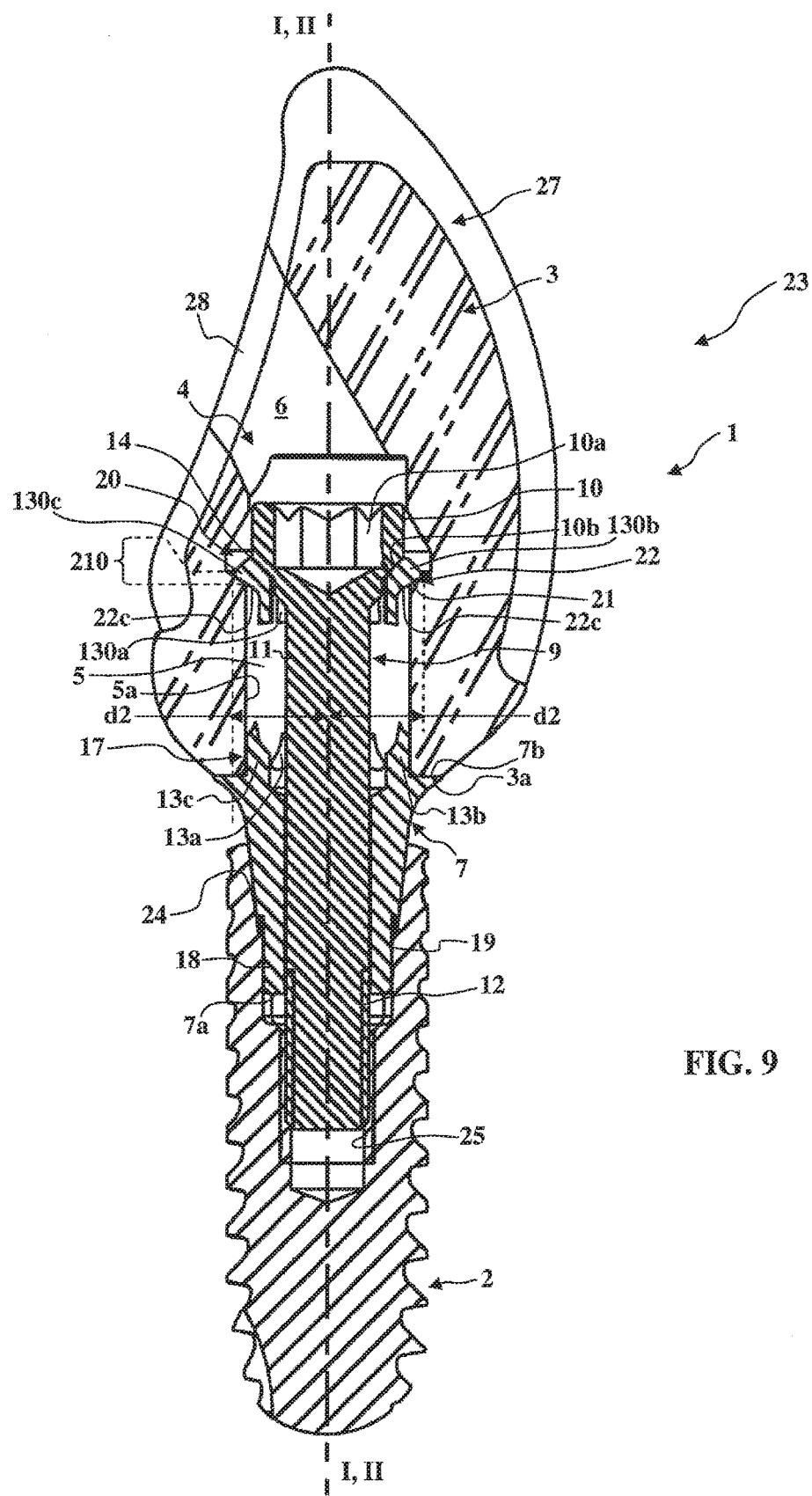
FIG. 9 is a view in cross section and from the side of the dental component of FIG. 1 assembled onto a dental implant to form a dental assembly, in which the first element is of the stratified dental prosthesis core type.

Three longitudinal fins 13a, 13b and 13c extend along the second longitudinal axis II-II from and away from the distal end 7b of the second element 7, each longitudinal fin 13a, 13b or 13c comprising a free distal part 130a to 130c displaceable radially away from the second longitudinal axis II-II. The screw shank 11 is able to pass through the second element 7 while being received between the longitudinal fins 13a to 13c and in the second through-passage 8 in order to be screwed into the dental implant 2, the screw head 10 then resting in axial abutment against the free distal parts 130a to 130c of the longitudinal fins 13a to 13c in order to retain the second element 7 on the dental implant 2 (FIG. 9). The first passage portion 5 of the first element 3 has transverse dimensions that allow the longitudinal fins 13a to 13c and the screw head 10 to be received by axial penetration along the first longitudinal axis I-I from the proximal end 3a of the first element 3. In this particular instance, the first passage portion 5 comprises, near the proximal end 3a, a minimum diameter D50 that is smaller than the diameter D130 of the free distal ends 130a to 130c. The longitudinal fins 13a to 13c are therefore received by means of a small radial displacement of the free distal parts 130a to 130c toward the second longitudinal axis II-II, as illustrated in FIG. 6.

The screw head 10 and the free distal parts 130a to 130c of the longitudinal fins 13a to 13c are configured in such a way that, when the first element 3 receives the longitudinal fins 13a to 13c and the screw head 10, a relative translational displacement of the fixing screw 9 toward the second element 7 along the second longitudinal axis II-II causes a radial displacement of the free distal parts 130a to 130c of the longitudinal fins 13a to 13c away from the second longitudinal axis II-II to press them against the lateral wall 5a of the first passage portion 5 so as to oppose withdrawal of the first element 3 away from the second element 7.

The second passage portion 5 has transverse dimensions (in this instance a diameter D6) smaller than those (diameter D5) of the first passage portion 5, but sufficient for the passage of a tool for turning the fixing screw 9 about the second longitudinal axis II-II.

More specifically, without this thereby constituting any limitation on the protection, the screw head 10 has a hollow screwing socket 10a of non-circular cross section, in this instance a hexagon socket.

In order to turn the fixing screw 9 about the second longitudinal axis II-II using a tool engaged at the angle A in the second passage portion 6, it is possible to use a hexagon key that allows a ball joint effect, such a key being well known to those skilled in the art. The socket 10a may also be designed in accordance with the teachings of document. EP 2 607 722 so as to allow the use of a turning driving tool that allows a ball joint effect.

It will be appreciated that the first passage portion 5 needs to have a minimal cross section of diameter D5 slightly greater than the outside diameter D10 of the screw head 10. For its part, the second passage portion 6 may have transverse dimensions (diameter D6 here) that are smaller than those of the first passage portion 5 because the turning driving tool used to turn the fixing screw 9 may itself have a cross section markedly smaller than the diameter D10 when all it has to do is enter the hollow socket 10a in the screw head 10. The first element 3, in the vicinity of the second passage portion 6, may therefore retain more constituent material and thus offer greater mechanical strength.

It may be seen more particularly in FIG. 2 that the screw head 10 has a substantially frustoconical contact surface 10b intended to come into contact against the free distal parts 130a to 130c of the longitudinal fins 13a to 13c. For their part, the free distal parts 130a to 130c of the longitudinal fins 13a to 13c comprise respective contact surfaces 131a to 131c which are intended to receive in abutment the screw head 10 and that form a substantially frustoconical surface 14. It should be noted that the contact surface 10b of the screw head 10 and the substantially frustoconical surface 14 formed by the respective contact surfaces 131a to 131c may, instead of having a rectilinear profile as illustrated in FIG. 2, have a curved (convex or concave) profile provided that a progressive reduction in cross section is similarly achieved. It is therefore notably possible to envision truncated spherical contact surfaces 10b and/or 14 (which are the intersection of a sphere between two substantially parallel planes). All these alternative forms of shape are considered to be covered by the expression "substantially frustoconical". The shapes of the contact surfaces 10b and 14 encourage the radial displacement of the free distal parts 130a to 130c away from the second longitudinal axis II-II when the fixing screw 9 undergoes a relative translational displacement toward the second element 7 when screwed into a dental implant 2.

Figure 3:
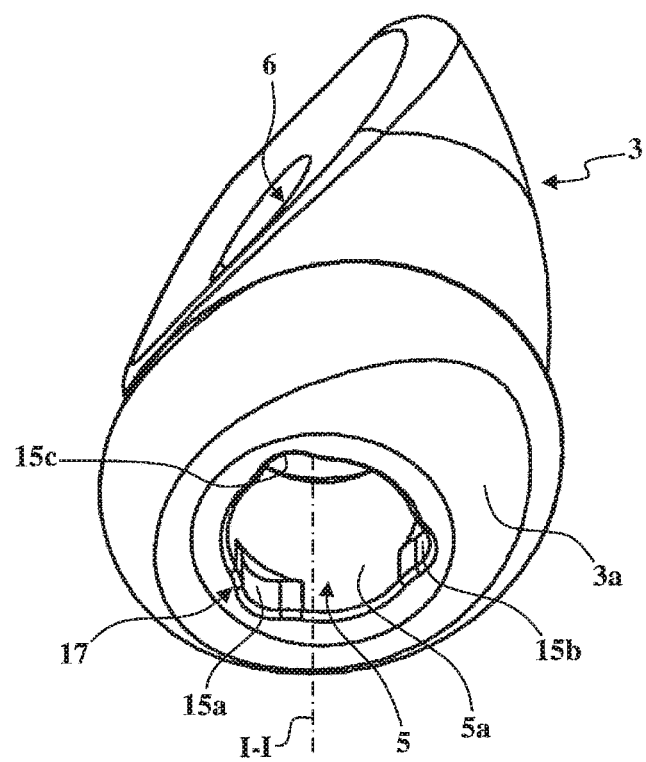
FIG. 3 is a perspective view from beneath of the first element of the dental component of FIG. 1.
Figure 4:
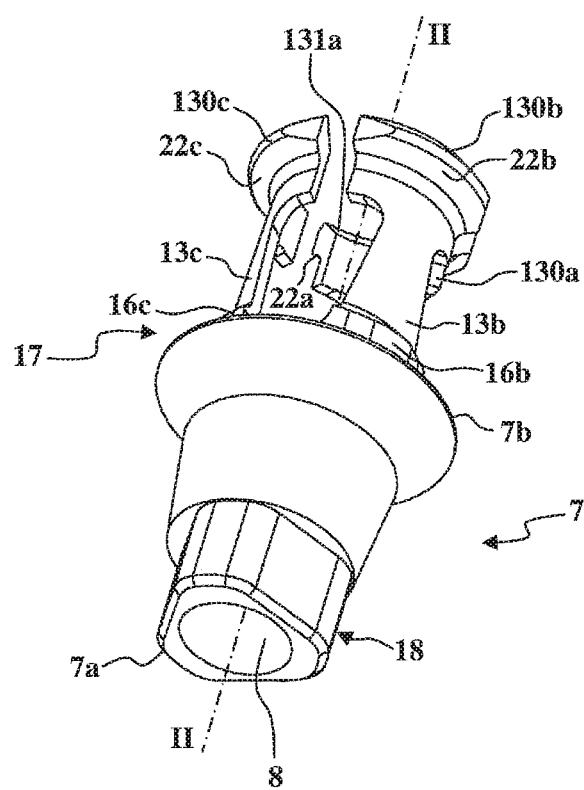
FIG. 4 is a perspective view from beneath of the second element of the dental component of FIG. 1.
Figure 5:
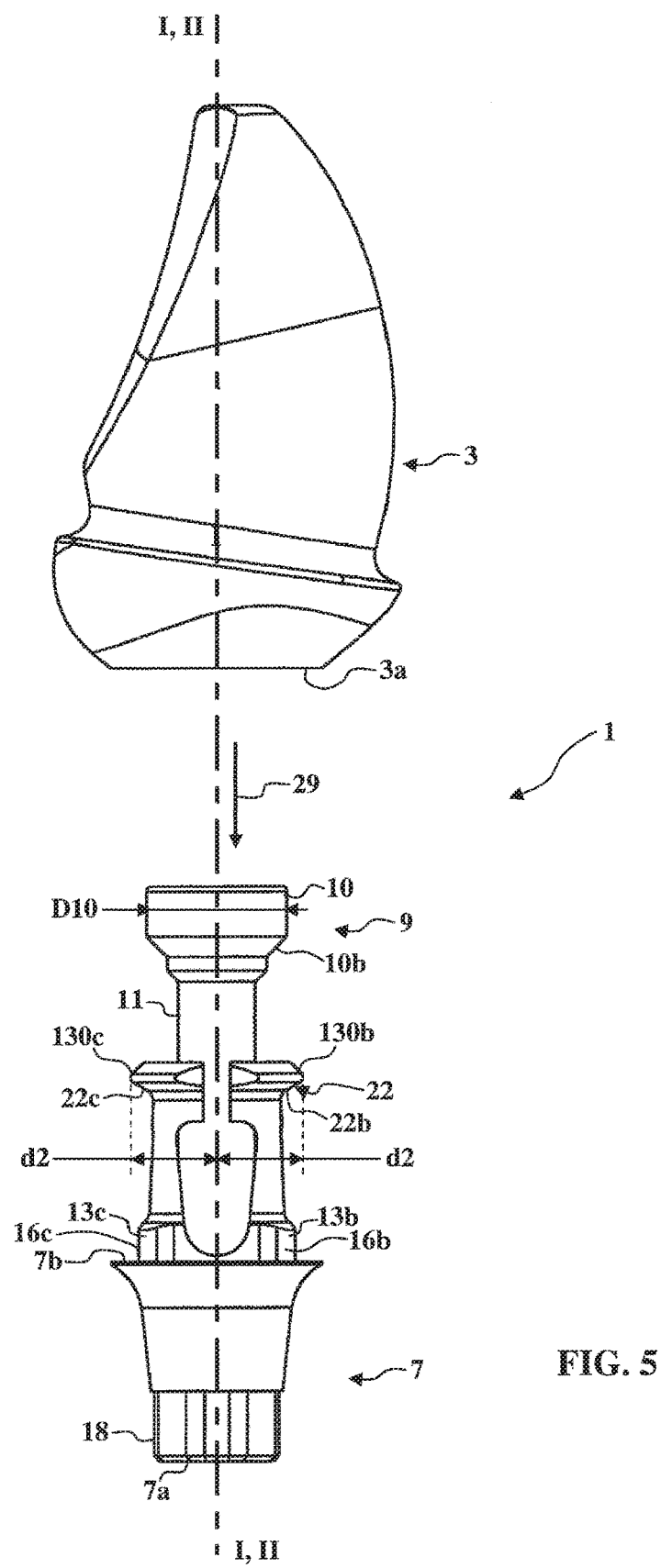
FIG. 5 is a side view of the dental component of FIG. 1 during the course of assembly.

It may be seen more particularly from FIGS. 3 and 4 that the first element 3 comprises, at the entry to the first passage portion 5, three radial housings 15a to 15c arranged 120° apart and intended to receive three corresponding pins 16a to 16c provided on the second element 7 at the base of the longitudinal fins 13a to 13c (because of the way in which the second element 7 is oriented, the pin 16a is not visible in FIG. 4). The radial housings 15a to 15c and the corresponding pins 16a to 16c constitute rotational-indexing means 17 for indexing the first and second elements 3 and 7 about the first longitudinal axis I-I (which coincide with the second longitudinal axis II-II when the first and second elements 3 and 7 are assembled).

It may also be seen from FIG. 4 that the second element 7 comprises a proximal appendage 18 of non-circular (substantially triangular with rounded vertexes) cross section intended to be received in a corresponding housing 19 (FIG. 8) of the dental implant 2, having a corresponding non-circular cross section. The proximal appendage 18 and the housing 19 collaborate to index the second element 7 with respect to the dental implant 2 in terms of rotation about the second longitudinal axis II-II.

Above the proximal appendage 18 there is a frustoconical portion intended to plug conically into the dental implant 2.

It may be seen more clearly from FIG. 2 that the first element 3 comprises a groove 20 intended to receive the free distal parts 130a to 130c of the longitudinal fins 13a to 13c during their radial displacement away from the second longitudinal axis The groove 20 and the screw head 10 comprise respective contact surfaces 21 and 22 which are configured so that the radial pressing of the free distal parts 130a to 130c of the longitudinal fins 13a to 13c against the groove 20 causes, along the first longitudinal axis I-I, a pressing of the proximal end 3a of the first element 3 against the distal end 7b of the second element 7. In this particular instance, the contact surface 21 of the groove 20 comprises a frustoconical portion 210, whereas the respective contact surfaces 22a to 22c of the free distal parts 130a to 130c form a substantially frustoconical surface 22. Once again, these surfaces referred to as "substantially frustoconical" are depicted as having a rectilinear profile, although this profile could equally be curved (concave or convex).

Figure 7:
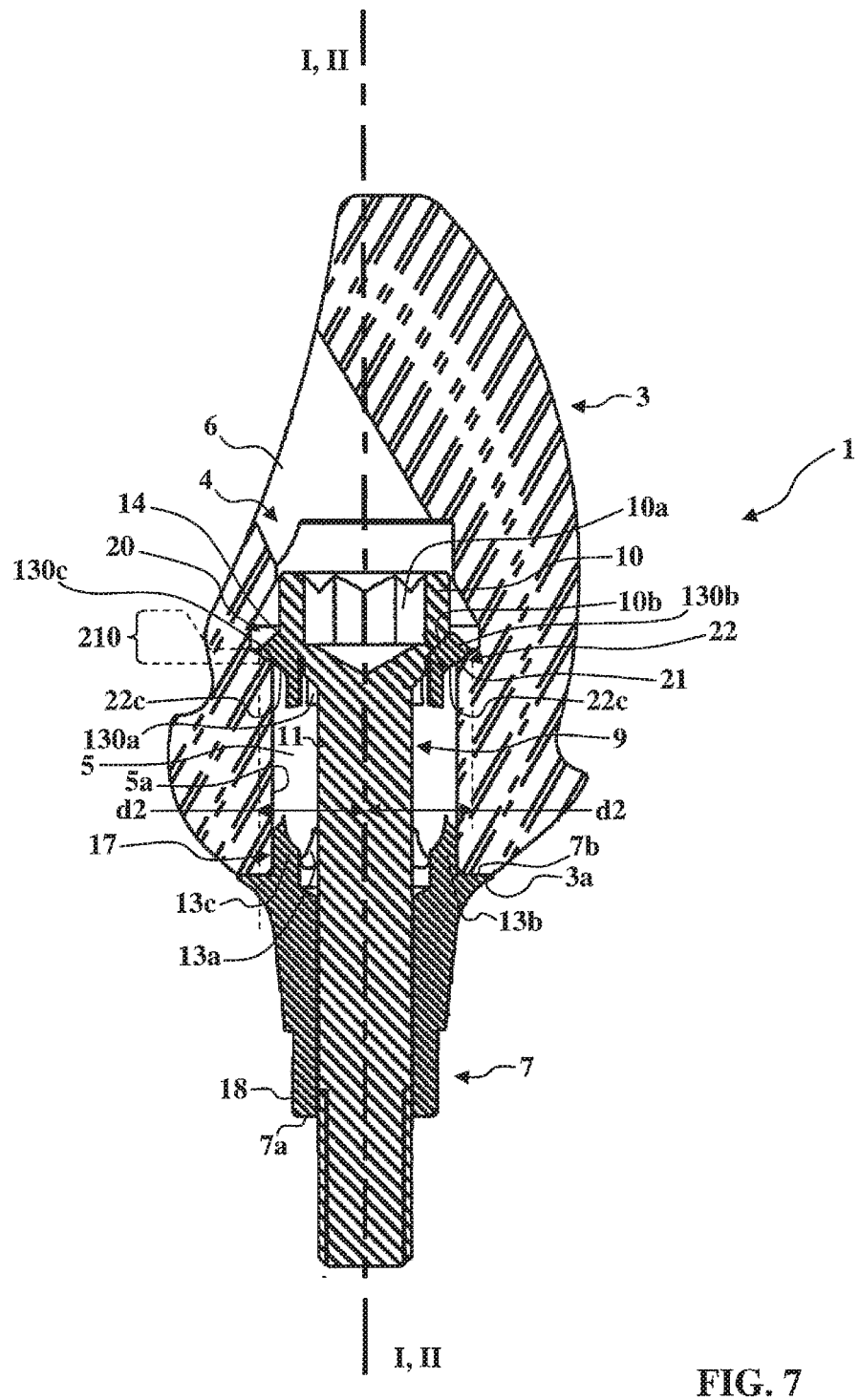
FIG. 7 is a view in cross section and from the side of the dental component of FIG. 1 during the course of assembly, at a later stage to the stage illustrated in FIG. 6.

It may be seen more particularly in FIG. 6 that the free distal parts 130a to 130c of the longitudinal fins 13a to 13c are displaceable between a closed-up position (FIG. 6) in which they are radially distant from the second longitudinal axis II-II by a first distance d1, and a spread position (FIG. 7) in which they are radially distant from the second longitudinal axis II-II by a second distance d2 greater than the first distance d1. The free distal parts 130a to 130c of the longitudinal fins 13a to 13c are elastically returned to the spread position (FIG. 7). The groove 20 and the longitudinal fins 13a to 13c are dimensioned and configured in such a way that the free distal parts 130a to 130c of the longitudinal fins 13a to 13c are received by snap-fastening in the groove when the first passage portion 5 receives the longitudinal fins 13a to 13b and the screw head by axial penetration along the first longitudinal axis I-I.

FIG. 8 illustrates dental assembly 23 comprising:
a dental component 1 as described hereinabove,
a dental implant 2 comprising an internal housing 24 with a threaded portion 25 intended to receive the fixing screw 9 by screwing.

In the embodiment illustrated in FIGS. 1 to 9, the first element 3 is a prosthesis core, made of metal or some other material, intended to be stratified. In FIG. 9, it may be seen that the stratification 27 performed by the prosthetist leaves the second passage portion 6 open. Once the dental component 1 has been fixed onto the dental implant 2 by means of the fixing screw 9, the dental surgeon can re-plug the orifice 28 providing access to the second passage portion 6 by injecting a suitable material into it.

Figure 10:
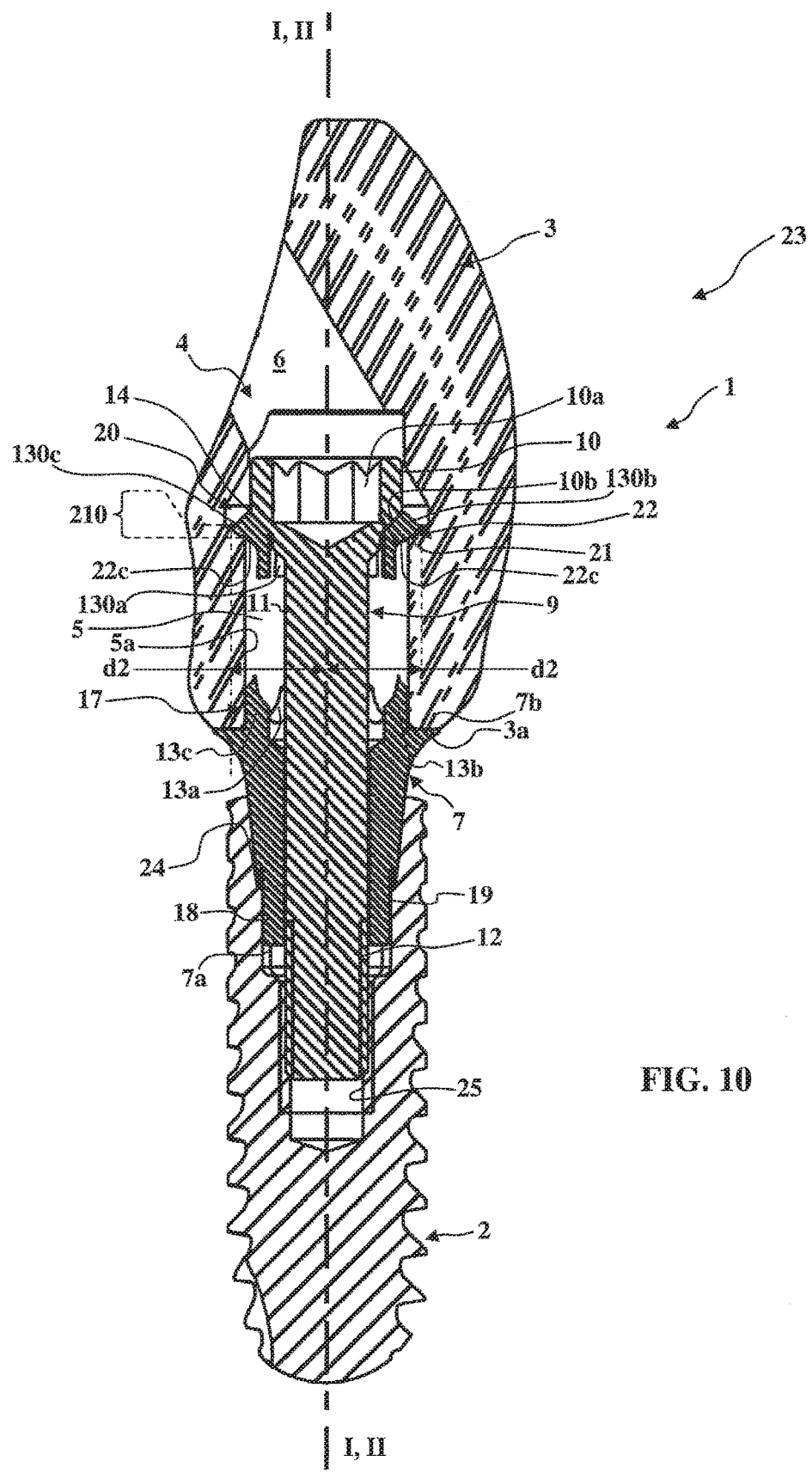
FIG. 10 is a view in cross section similar to that of FIG. 9, in which the first element is of the monoblock (sintered or machined) ceramic dental prosthesis core type.

The second embodiment illustrated in FIG. 10 differs from the first embodiment illustrated in FIG. 9 only in that the first element 3 is a dental prosthesis monoblock ceramic core. This monoblock ceramic core may be obtained by machining from a solid block of ceramic or may be obtained by sintering a powder. The monoblock ceramic core may also have on its exterior surface a light layer of a material such as a lacquer that gives it a look better suited to the patient's dentition (for example in terms of coloration if the patient has yellowish teeth). Once again, as in the first embodiment illustrated in FIG. 9, the second passage portion is plugged by the dental surgeon after the dental component 1 has been added and fixed to the dental implant 2 by means of the fixing screw 9.

The use of the dental component 1 according to the invention will now be explained using FIGS. 2 and 5 to 9.

For the individual prosthetic reconstruction of one of the patient's teeth, the prosthetist takes a second element 7 and a fixing screw 9 which are standard elements corresponding to a dental implant 2 osteointegrated into the jaw of the patient. The first element 3 is an element that is custom-made for the patient by the prosthetist, preferably using three-dimensional machining.

Once the first element 3 has been manufactured by the prosthetist, he may perform the ex-vivo assembly of the dental component 1. To do that, the prosthetist inserts the screw shank 11 between the longitudinal fins 13a to 13c and into the second through-passage 8 (which movement is illustrated by the arrow 29 in FIG. 5).

The prosthetist next inserts the longitudinal fins 13a to 13c and the screw head 10 into the first passage portion 5 through an axial translational movement (illustrated by the arrow 30 in FIG. 6) along the first longitudinal axis I-I from the proximal end 3a of the first element 3. In order to allow this insertion, the free distal parts 130a to 130c are displaced elastically from their spread position (FIG. 5) toward a closed-up position (FIG. 6). The prosthetist then continues the axial translational movement (arrow 30 in FIG. 6) until the free distal parts 130a to 130c of the longitudinal fins 13a to 13c snap-fasten into the groove 20 (FIG. 7). During this insertion, the pins 16a to 16c are received in the housings 15a to 15c to rotationally index the first and second elements 7 about the first longitudinal axis I-I.

This then yields the assembled dental component 1 as illustrated in FIG. 7.

The prosthetist next performs stratification of the first element 3, leaving the second passage portion 6 open. During this stratification, the dental component 1 is generally installed on a master model. The prosthetist applies a material to the first element 3 in one or more layers to yield an appearance as close as possible to that of a natural tooth, while taking the adjacent teeth into consideration.

Each layer has to be baked in the oven. To do that, the prosthetist removes the dental component 1 from the master model and easily detaches the stratified first element 3 from the second element 7 and the fixing screw 9 because of the reversible engagement of the free distal parts 130a-130c of the longitudinal fins 13a-13c in the groove 20. The first element 3 is then placed in the oven to bake the applied layer of material. The second element 7 and the fixing screw 9 are not put into the oven, in order to prevent them from oxidizing. An oxidized second element 7 could cause the gums to recede. Furthermore, oxidation of the second element 7 and/or of the fixing screw 9 would reduce its(their) mechanical strength.

Once the first element 3 has been stratified by the prosthetist, he may perform a final ex-vivo assembly of the dental component 1 before then sending the assembled dental component 1 to the dental surgeon who will install it in the patient's mouth. To do that, as illustrated in FIG. 8, the dental surgeon inserts the second element 7 (which may sometimes be qualified as a "base") into the internal housing 24 of the dental implant 2. During this insertion, the proximal appendage 18 collaborates with the housing 19 of the dental implant 2 to index the dental component 1 in terms of rotation about the second longitudinal axis II-II. The frustoconical portion situated above, the proximal appendage 18 plugs conically into frustoconical land of corresponding shape situated above the housing 19 of non-circular cross section of the dental implant 2. This conical plugging-together contributes to the good stability of the assembly.

The dental surgeon then inserts into the second passage portion 6 a tool (in this instance a hexagon key) until its end enters the hollow socket 10a in the screw head 10, allowing the fixing screw 9 to be turned. The dental surgeon then screws the fixing screw 9 into the threaded portion 25 of the dental implant 2, this having the effect of causing relative translational displacement of the fixing screw 9 toward the second element 7 along the second longitudinal axis II-II. Because of the shaping of the screw head 10 and of the free distal parts 130a to 130c of the longitudinal fins 13a to 13c, this translational displacement of the fixing screw 9 causes a radial displacement of the free distal parts 130a to 130c away from the second longitudinal axis II-II to press them against the lateral wall 5a of the first passage portion 5. As a result of this, the screwing of the fixing screw 9 presses the contact surfaces 21 (of the groove 20) and 22a to 22c (of the free distal parts 130a to 130c) against one another. The radial pressing of the free distal parts 130a to 130c against the groove 20 causes, along the first longitudinal axis and because of the orientation of the contact surfaces 21 and 22a to 22c, a pressing of the proximal end 3a of the first element 3 against the distal end 7b of the second element 7. This pressing makes it possible to ensure a good seal at the interface between the first and second elements 3 and 7 so as to prevent bacterial growth there. This then is the configuration illustrated in FIG. 9.

Finally, the dental surgeon plugs the orifice 28 of the second passage portion 6 using a suitable material.

The use of the dental components illustrated in FIG. 10 is in every respect similar to the use described previously of the dental component 1 of FIGS. 1 to 9. In this embodiment, the first element 3 may also undergo (optional) stratification by the application by the prosthetist of one or more very light texturing or coloration layers yielding an appearance as close as possible to that of a natural tooth.

In the context of the second embodiment of the present invention with a first element 3 taking the form of a ceramic core (machined from a block of ceramic or produced by sintering notably a ceramic powder), the second element 7 allows the first element 3 to be added and fixed to the dental implant 2 without direct contact between the first element 3 and the dental implant 2. The second element 7 acts as a spacer. This then avoids relative micromovements between the first element 3 and the dental implant 2 leading to premature wearing of the dental implant 2 which is osteointegrated and which it is therefore necessary to avoid having to replace. This is of quite particular importance when the dental implant 2 is made not of ceramic (but for example of metal, titanium or titanium alloy in particular). If micromovements between the first element 3 and the second element 7 occur that cause premature, wearing of the latter, the second element 7 can quickly and easily be replaced.

The present invention is not restricted to the embodiments explicitly described but includes the various alternative forms and generalizations thereof included within the scope of the claims which follow.

The invention claimed is:

1. A dental component for the individual prosthetic reconstruction of a tooth, intended to be received on a dental implant, comprising:
   a first element being a core on which stratification is performed or being a ceramic core, said first element having a first through-passage made up of first and second successive passage portions, said first passage portion extending from a proximal end of the first element along a first longitudinal axis, and said second passage portion extending the first passage portion in such a way that the first and second passage portions form between them a non-zero angle,
a second element with a second through-passage extending along a second longitudinal axis, comprising a distal end intended to receive in abutment the first element, and comprising a proximal end intended to bear in axial abutment against or intended to penetrate into said dental implant,
a fixing screw comprising a screw head from which there extends a screw shank provided with a threaded portion intended to be received by screwing in said dental implant,
several longitudinal fins extending along the second longitudinal axis from and away from the distal end of the second element, each longitudinal fin comprising a free distal part that can be moved radially away from the second longitudinal axis,
wherein:
the screw shank is able to pass through the second element by being received between the longitudinal fins and into the second through-passage in order to screw into the dental implant, whereas the screw head then comes to rest in axial abutment against the free distal parts of the longitudinal fins to retain the second element on the dental implant,
the first passage portion of the first element has transverse dimensions allowing the longitudinal fins and the screw head to be received by axial penetration along the first longitudinal axis from the proximal end of the first element,
the screw head and the free distal parts of the longitudinal fins are configured in such a way that, when the first element receives the longitudinal fins and the screw head, a relative translational displacement of the fixing screw toward the second element along the second longitudinal axis causes a radial displacement of the free distal parts of the longitudinal fins away from the second longitudinal axis in order to press them against a lateral wall of the first passage portion in order to oppose a withdrawal of the first element away from the second element,
the second passage portion of the first element has transverse dimensions smaller than those of the first passage portion, but sufficient for the passage of a tool that allows the fixing screw to be turned about the second longitudinal axis.

2. The dental component as claimed in claim 1, wherein the screw head comprises a substantially frustoconical contact surface intended to come into contact against the free distal parts of the longitudinal fins and/or the free distal parts of the longitudinal fins comprise respective contact surfaces intended to receive in abutment the screw head and forming a substantially frustoconical surface.

3. The dental component as claimed in claim 1, comprising rotational-indexing means for indexing the first and second elements about the first longitudinal axis.

4. The dental component as claimed in claim 1, wherein the second element comprises a proximal appendage of non-circular cross section which is intended to be received in a housing of non-circular cross section of the dental implant.

5. The dental component as claimed in claim 1, wherein the first element is a dental prosthesis core intended to be stratified.

6. The dental component as claimed in claim 1, wherein the first element is a dental prosthesis ceramic monoblock core.

7. The dental component as claimed in claim 1, wherein the screw head comprises a hollow screwing socket of non-circular cross section.

8. The dental component as claimed in claim 1, wherein the first element comprises a groove intended to receive the free distal parts of the longitudinal fins during their radial displacement away from the second longitudinal axis.

9. The dental component as claimed in claim 8, wherein the free distal parts of the longitudinal fins are received in the groove via reversible engagement.

10. The dental component as claimed in claim 8, wherein the groove and/or the free distal parts of the longitudinal fins comprise respective contact surfaces which are configured in such a way that the radial pressing of the free distal parts of the longitudinal fins against the groove causes, along the first longitudinal axis, a pressing of the proximal end of the first element against the distal end of the second element.

11. The dental component as claimed in claim 8, wherein:
the free distal parts of the longitudinal fins are displaceable between a closed-up position in which they are radially distant from the second longitudinal axis by a first distance, and a spread position in which they are radially distant from the second longitudinal axis by a second distance greater than the first distance,
the longitudinal fins are elastic,
the free distal parts of the longitudinal fins are elastically urged to the spread position,
the groove and the longitudinal fins are dimensioned and configured in such a way that the free distal parts of the longitudinal fins are received by snap-fastening in the groove when the first passage portion receives the longitudinal fins and the screw head by axial penetration along the first longitudinal axis.

12. A dental assembly comprising:
a dental implant,
a dental component, intended to be received on said dental implant,
the dental component comprising:
a first element being a core on which stratification is performed or being a ceramic core, said first element having a first through-passage made up of first and second successive passage portions, said first passage portion extending from a proximal end of the first element along a first longitudinal axis, and said second passage portion extending the first passage portion in such a way that the first and second passage portions form between them a non-zero angle,
a second element with a second through-passage extending along a second longitudinal axis, comprising a distal end intended to receive in abutment the first element, and comprising a proximal end intended to bear in axial abutment against or intended to penetrate into said dental implant,
a fixing screw comprising a screw head from which there extends a screw shank provided with a threaded portion intended to be received by screwing in said dental implant,
several longitudinal fins extending along the second longitudinal axis from and away from the distal end of the second element, each longitudinal fin comprising a free distal part that can be moved radially away from the second longitudinal axis, wherein:
the screw shank is able to pass through the second element by being received between the longitudinal fins and into the second through-passage in order to screw into the dental implant, whereas the screw head then comes to rest in axial abutment against the free distal parts of the longitudinal fins to retain the second element on the dental implant,
the first passage portion of the first element has transverse dimensions allowing the longitudinal fins and the screw head to be received by axial penetration along the first longitudinal axis from the proximal end of the first element,
the screw head and the free distal parts of the longitudinal fins are configured in such a way that, when the first element receives the longitudinal fins and the screw head, a relative translational displacement of the fixing screw toward the second element along the second longitudinal axis causes a radial displacement of the free distal parts of the longitudinal fins away from the second longitudinal axis in order to press them against a lateral wall of the first passage portion in order to oppose a withdrawal of the first element away from the second element,
the second passage portion of the first element has transverse dimensions smaller than those of the first passage portion, but sufficient for the passage of a tool that allows the fixing screw to be turned about the second longitudinal axis,
wherein said dental implant comprises an internal housing with a threaded portion intended to receive the fixing screw of the dental component by screwing.

13. A method for the ex-vivo assembly of a dental component the dental component comprising:
a first element being a core on which stratification is performed or being a ceramic core, said first element having a first through-passage made up of first and second successive passage portions, said first passage portion extending from a proximal end of the first element along a first longitudinal axis, and said second passage portion extending the first passage portion in such a way that the first and second passage portions form between them a non-zero angle,
a second element with a second through-passage extending along a second longitudinal axis, comprising a distal end intended to receive in abutment the first element, and comprising a proximal end intended to bear in axial abutment against or intended to penetrate into said dental implant,
a fixing screw comprising a screw head from which there extends a screw shank provided with a threaded portion intended to be received by screwing in said dental implant,
several longitudinal fins extending along the second longitudinal axis from and away from the distal end of the second element, each longitudinal fin comprising a free distal part that can be moved radially away from the second longitudinal axis, wherein:
the screw shank is able to pass through the second element by being received between the longitudinal fins and into the second through-passage in order to screw into the dental implant, whereas the screw head then comes to rest in axial abutment against the free distal parts of the longitudinal fins to retain the second element on the dental implant,
the first passage portion of the first element has transverse dimensions allowing the longitudinal fins and the screw head to be received by axial penetration along the first longitudinal axis from the proximal end of the first element,
the screw head and the free distal parts of the longitudinal fins are configured in such a way that, when the first element receives the longitudinal fins and the screw head, a relative translational displacement of the fixing screw toward the second element along the second longitudinal axis causes a radial displacement of the free distal parts of the longitudinal fins away from the second longitudinal axis in order to press them against a lateral wall of the first passage portion in order to oppose a withdrawal of the first element away from the second element,
the second passage portion of the first element has transverse dimensions smaller than those of the first passage portion, but sufficient for the passage of a tool that allows the fixing screw to be turned about the second longitudinal axis,
wherein the first element comprises a groove intended to receive the free distal parts of the longitudinal fins during their radial displacement away from the second longitudinal axis,
and wherein:
the free distal parts of the longitudinal fins are displaceable between a closed-up position in which they are radially distant from the second longitudinal axis by a first distance, and a spread position in which they are radially distant from the second longitudinal axis by a second distance greater than the first distance,
the longitudinal fins are elastic,
the free distal parts of the longitudinal fins are elastically urged to the spread position,
the groove and the longitudinal fins are dimensioned and configured in such a way that the free distal parts of the longitudinal fins are received by snap-fastening in the groove when the first passage portion receives the longitudinal fins and the screw head by axial penetration along the first longitudinal axis,
the method comprising the following steps:
a) inserting the screw shank between the longitudinal fins and into the second through-passage,
b) inserting into the first passage portion the longitudinal fins and the screw head through an axial translational movement along the first longitudinal axis from the proximal end of the first element until the free distal parts of the longitudinal fins snap-fasten into the groove.

* * * * *

UNITED STATES PATENT AND TRADEMARK OFFICE
CERTIFICATE OF CORRECTION

PATENT NO. : 10,010,384 B2  
APPLICATION NO. : 15/408584  
DATED : July 3, 2018  
INVENTOR(S) : Hervé Richard Page 1 of 1

It is certified that error appears in the above-identified patent and that said Letters Patent is hereby corrected as shown below:

In the Specification

Column 6, Line 63, delete "second passage portion 5" and insert instead --second passage portion 6--.

Signed and Sealed this  
Eighteenth Day of September, 2018

Andrei Iancu  
*Director of the United States Patent and Trademark Office*